(12) United States Patent
Hildebrandt

(10) Patent No.: US 11,439,729 B2
(45) Date of Patent: Sep. 13, 2022

(54) IMPLANTABLE MEDICAL PRODUCT WITH PERMANENTLY NEGATIVELY CHARGED SURFACE

(71) Applicant: UroNova GmbH medizinische Implantate, Erlangen (DE)

(72) Inventor: Peter Hildebrandt, Herzogenaurach (DE)

(73) Assignee: URONOVA GMBH MEDIZINISCHE IMPLANTATE, Erlangen (DE)

( * ) Notice: Subject to any disclaimer, the term of this patent is extended or adjusted under 35 U.S.C. 154(b) by 0 days.

(21) Appl. No.: 16/546,693

(22) Filed: Aug. 21, 2019

(65) Prior Publication Data
US 2020/0061243 A1  Feb. 27, 2020

(30) Foreign Application Priority Data
Aug. 23, 2018 (DE) ............ 10 2018 214 299.8

(51) Int. Cl.
*A61L 27/34* (2006.01)
*A61K 31/09* (2006.01)
*A61K 38/46* (2006.01)

(52) U.S. Cl.
CPC .......... *A61L 27/34* (2013.01); *A61K 31/09* (2013.01); *A61K 38/46* (2013.01); *A61F 2310/0097* (2013.01); *A61L 2300/202* (2013.01); *A61L 2300/254* (2013.01); *A61L 2300/404* (2013.01)

(58) Field of Classification Search
CPC ........ A61L 27/54; A61L 31/088; A61L 29/10; A61L 27/30; A61L 27/32; A61L 27/306; A61L 31/16; A61L 29/16; A61L 31/082; A61L 27/34; A61L 29/106; A61L 31/086; A61L 2300/80; A61L 2300/10; A61L 2420/02; A61L 2300/254; A61L 2300/424; A61L 2300/404; A61L 2300/112; A61L 2300/202; A61K 31/09; A61K 38/46; A61F 2310/0097
See application file for complete search history.

(56) References Cited

U.S. PATENT DOCUMENTS

| | | | |
|---|---|---|---|
| 4,882,148 A | 11/1989 | Pinchuk | |
| 5,718,726 A | 2/1998 | Amon et al. | |
| 5,939,208 A | 8/1999 | Stoy | |
| 2001/0037144 A1* | 11/2001 | Kim | B82Y 30/00 623/1.15 |
| 2011/0135703 A1 | 6/2011 | Shipp | |
| 2014/0218797 A1* | 8/2014 | Mochizuki | C09B 45/28 359/487.02 |

FOREIGN PATENT DOCUMENTS

| | | | |
|---|---|---|---|
| AU | 2013245551 B2 | 2/2016 | |
| DE | 26 22 394 A1 | 12/1976 | |
| EP | 0 761 244 A2 | 3/1973 | |
| EP | 0239847 A1 * | 10/1987 | C09B 62/51 |
| EP | 0890367 A2 | 1/1999 | |
| GB | 1 504 101 | 3/1978 | |
| WO | 2005/032417 A2 | 4/2005 | |

OTHER PUBLICATIONS

Tenke et al. "Bacterial biofilm formation on urologic devices and heparin coating as preventive strategy," in International Journal of Antimicrobial Agents 23S1 (2004) S67-S74.*
Liao et al. ("Covalent linkage of heparin provides a stable anti-coagulation surface of decellularized porcine arteries," in J. Cell. Mol. Med. vol. 13, No. 8B, 2009 pp. 2736-2743).*
Shethal AnilKumar et al., "Fabrication of Antibacterial Coatings: Prevention of Implant Associated Infections in Patients Indwelling Urinary Catheters", IOSR Journal of Pharmacy and Biological Sciences, vol. 10, pp. 82-89 (Dec. 2015).
Balazs, et al., Inhibition of bacterial adhesion on PVC endotracheal tubes by RF-oxygen glow discharge, sodium hydroxide and silver nitrate treatments, Biomaterials, 2004, pp. 2139-2152, vol. 25.
Cheng, et al., Inhibition of bacterial adhesion and biofilm formation on zwitterionic surfaces, Biomaterials, 2007, pp. 4192-4199, vol. 28.
Emerson, et al., Microscale Correlation between Surface Chemistry, Texture, and the Adhesive Strength of *Staphylococcus epidermidis*, Langmuir, 2006, pp. 11311-11321, vol. 22.

* cited by examiner

*Primary Examiner* — Blessing M Fubara
(74) *Attorney, Agent, or Firm* — Browdy and Neimark, PLLC

(57) ABSTRACT

An entirely or partially implantable medical product with a negatively charged surface for repulsing bacteria has a superficially bonded substance with a permanently negative excess charge, which substance is inert against cells of the human body and the bacteria contained therein.

3 Claims, No Drawings

IMPLANTABLE MEDICAL PRODUCT WITH PERMANENTLY NEGATIVELY CHARGED SURFACE

This application claims the priority of German Patent Application, Serial No. DE 10 2018 214 299.8, filed on Aug. 23, 2018, pursuant to 35 U.S.C. 119(a)-(d), the content of which is incorporated herein by reference in its entirety as if fully set forth herein.

FIELD OF THE INVENTION

The invention relates to an entirely or partially implantable medical product with a negatively charged surface for repulsing bacteria.

BACKGROUND OF THE INVENTION

The background of the invention is to be explained as follows. The colonization of implantable medical products with bacteria, biofilm and incrustations and the problems resulting therefrom during patient care have been the object of research for many years. As examples for such implantable medical products, stents, catheters, mesh implants, breast implants and heart pacemakers can be named, wherein there is a large number of further examples. Bacterial colonization may lead to the formation of biofilm and infections, furthermore it causes other effects, such as the occlusion of tube-like implants by accumulations and incrustation. Bonding pharmacological substances to the surface of implantable medical products has partially proven to be successful in this context. Thus, numerous documents can be retrieved from the state of the art, which, for example, suggest a covalent bonding of antibiotic substances to the surface, like for example in US 2011/135703 A1 and AU 2013245551 B2.

In the patent El 0 890 367 131, the covalent bonding of glycosaminoglycans to a urologic implant is suggested. As later research works have shown, this concept has indeed proven to be successful. The negative charge of the glycosaminoglycans is considered to be a decisive factor for the effectiveness (Int J Antimicrob Agents, 2004, 23: Bacterial biofilm formation on urologic devices and heparin coating as preventive strategy. Tenke P. et al.). Since bacteria have a negative excess charge, as well, there is an electrostatic repulsion by the surface coated with glycosaminoglycans. Heparin is the glycosaminoglycan with the highest negative charge, in this context. The negative charge of the bacteria, in the case of gram-negative bacteria, is due to the strongly negatively charged lipopolysaccharides in the cell wall, in the case of gram-positive bacteria, is due to the negatively charged phosphate group of the phosphodiester bonds between the monomers of the teichoic acids in the cell wall.

In addition to the general prior art, reference is to be made to the specialized publication of Shetal AnilKumar et al., "Fabrication of Antibacterial Coatings: Prevention of Implant Associated Infections in Patients Indwelling Urinary Catheters", Journal of Pharmacy and Biological Sciences, Vol. 10, Issue 6 ver. III (November-December 2015), p. 82-89.

However, bonding substances with pharmacological effect also causes different issues. A pharmacological effect is to be understood as a reciprocal effect between the substance and a cellular component of the patient's body or a cellular component existing in the patient's body. The latter, for example, are bacteria or fungi in the patient's body, which, for example, interact with biocidal or antibiotic substances. Besides the desired effect of obtaining a negatively charged surface for repulsing bacteria, an undesired effect may be caused in addition, due to the bonding of pharmacological substances. When using the glycosaminoglycans heparin and heparan sulfate, this may be the anticoagulant effect, which, for example with percutaneous catheters such as nephrostomy catheters or suprapubic urinary catheters, may lead to an increased bleeding tendency, which is an obstacle to the use of catheters that are equipped in such a way. In the case of the glycosaminoglycan hyaluronic acid, a boosting effect regarding the cell proliferation has been detected and it is used in preparations for the conservation of the joint function. The influence on the cell proliferation may, for example, lead to undesired effects to vascular wall supports, such as an overgrowth of same by proliferating tissue.

Another issue is the classification of medical products. In certain countries, medical products, to whose surface pharmacological substances are bonded even if this bonding is carried out to be long-term stable and without the danger of setting free substances—are classified as combination products. As a consequence, directives regarding pharmaceutical products have to be followed and the effort for marketing authorization and distribution is increasing significantly.

Against this background, the prior art represents itself to be worthy of improvement.

SUMMARY OF THE INVENTION

In order to resolve the problems described of the prior art, the invention suggests the basic principle of bonding a substance with a permanently negative excess charge superficially, which substance is inert against the cells of the human body and the bacteria contained therein. By this means, a modification of the surface of an implantable medical product for the creation of a permanent negative charge is realized without using substances which have a pharmacological or other adverse effect. Thus, the problems described at the beginning are entirely avoided without loss in effectiveness.

For the superficially bonded substance, different possibilities of implementation are given. Very basically, attention has to be paid to the fact that this substance maintains its negative excess charge on the surface permanently and that its negative charge is not neutralized by chemical reactions in the implantation area. Such reactions may take place, for example, when there is contact with tissue and body fluids such as blood, urine or wound secretions.

DESCRIPTION OF THE PREFERRED EMBODIMENTS

For such a basic substance, different advantageous variants arise. The invention suggests in this case to bond one or more different carboxylic acids to the surface. With the help of alkaline solutions, the charge-balanced carboxyl groups of the carboxylic acids can be deprotonated and thus be transformed into a negatively charged carboxylate group. By establishing a mesomerism, a stabilization of the negative charge is achieved. Thus, the desired permanent negative charge of the surface is achieved without having to accept a pharmacological effect disturbing in many applications. As an alternative to the carboxylic acids, for example, also sulfonic acids and phosphorous acids are to be named, which can be deprotonated, as well, and stabilize their negative charge due to the establishment of a mesomerism.

A selection of carboxylic acids with no pharmacological effect are oxalic acid, tricarballylic acid and mellitic acid, wherein the first one is a dicarboxylic acid, the second one is a tricarboxylic acid and the last one is a hexacarboxylic acid. Due to the six carboxyl groups, hexacarboxylic acids seem to be most suitable, as an especially high negative charge can he achieved. In deprotonated state, these substances are PH-neutral and have no effect on biological organisms.

A suitable substitute of sulfonic acids is, for example, 6-aminonaphthalene-2-sulfonic acid, which has an amino group and thus can be bonded covalently via a peptide bond.

An appropriate substitute of phosphonic acids is, for example, (3-aminopropyl)phosphonic acid, which has an amino group, as well, and thus can be bonded covalently via a peptide bond.

In order to achieve a long-term stable bond to the surface of the medical product, a covalent bonding is suggested, as in the form of a peptide bond. However, other types of bonding are also possible, as for example an ionic bond.

Another preferred embodiment provides for a deprotonation of the substance by means of diluted sodium hydroxide solution.

Below, more details will be described with the invention and reference to different

Exemplary Embodiments

Example I—Covalent Coating Process with Tricarballylic Acid on a Medical Implant with Silicone Surface 1) To this end, the silicone surface, in order to prepare it for the bonding of tricarballylic acid, is immersed in an aqueous 3-aminopropyltriethoxysilane solution for 12 h and afterwards rinsed in deionized water.
2) For bonding the tricarballylic acid via a peptide bond, the such prepared silicone surface is immersed in an aqueous solution of tricarballylic acid and N-(3-dimethylaminopropyl)-N'-ethylcarbodiimide for 1 h and afterwards rinsed in deionized water.
3) For the deprotonation of the free carboxyl group of the tricarballylic acid, the such prepared silicone surface is now immersed in a 10 percent sodium hydroxide solution for 6 h and afterwards rinsed in deionized water.

Example II—Covalent Coating Process with 6-aminonaphthalene-2-sulfonic Acid on a Polyurethane Surface 1) To this end, the polyurethane surface, in order to prepare it for the bonding of taurine, is immersed in a hexamethylene diisocyanate solution in ether for 12 h and afterwards rinsed in deionized water.
2) The such prepared polyurethane surface is then immersed for hydrolysis in an aqueous solution of sodium hydrogen carbonate for 12 h and afterwards rinsed in deionized water.
3) The such prepared polyurethane surface is then immersed in an aqueous solution of malonic acid and N-(3-dimethylaminopropyl)-N'-ethylcarbodiimide for 12 h and afterwards rinsed in deionized water.
4) The such prepared polyurethane surface, in order to prepare it for the bonding of taurine, is immersed in an aqueous solution of N-(3-dimethylaminopropyl)-N'-ethylcarbodiimide for 1 h.
5) For bonding 6-aminonaphthalene-2-sulfonic acid via a peptide bond, the such prepared polyurethane surface is immersed in an aqueous solution of 6-aminonaphthalene-2-sulfonic acid for 12 h and afterwards rinsed in deionized water.
6) For the deprotonation of the free sulfonic acid groups of the 6-aminonaphthalene-2-sulfonic acid, the such prepared polyurethane surface is now immersed in a 10 percent sodium hydroxide solution for 6 h and afterwards rinsed in deionized water.

Example III—Covalent Coating Process with (3-aminopropyl)phosphonic Acid on a Polyurethane Surface 1) To this end, the polyurethane surface, in order to prepare it for the bonding of (3-aminopropyl)phosphonic acid, is immersed in a hex-amethylene diisocyanate solution in ether for 12 h and afterwards rinsed in deionized water.
2) The such prepared polyurethane surface is then immersed for hydrolysis in an aqueous solution of sodium hydrogen carbonate for 12 h and afterwards rinsed in deionized water.
3) The such prepared polyurethane surface is then immersed in an aqueous solution of malonic acid and N-(3-dimethylaminopropyl)-N'-ethylcarbodiimide for 12 h and afterwards rinsed in deionized water.
4) The such prepared polyurethane surface, in order to prepare it for the bonding of (3-aminopropyl)phosphonic acid, is immersed in an aqueous solution of N-(3-dimethylaminopropyl)-N'-ethylcarbodiimide for 1 h.
5) For bonding (3-aminopropyl)phosphonic acid via a peptide bond, the such prepared polyurethane surface is immersed in an aqueous solution of (3-aminopropyl)phosphonic acid for 12 h and afterwards rinsed in deionized water.
6) For the deprotonation of the free sulfonic acid groups of the 6-aminonaphthalene-2-sulfonic acid, the such prepared polyurethane surface is now immersed in a 10 percent sodium hydroxide solution for 6 h and afterwards rinsed in deionized water.

Detection Test Regarding Example I—Long-Term Stable Bonding of Tricarballylic Acid with Negatively Charged Carboxylate Group on Silicone Surface The test is carried out with the help of toluidine blue. The latter is a positively colored dye which ionically bonds to the negatively charged carboxylate groups. For detecting a long-term stable bonding of tricarballylic acid with negatively charged carboxylate groups according to the method described above, the following steps have been carried out:

A) Rinsing the samples gained from example I for 7 days in physiologic saline solution for removing adsorbed, non-covalent bonded tricarballylic acid under permanent circulation with the help of a magnetic stirrer.
B) Preparing a 0.1 percent aqueous solution of toluidine blue and measuring the transmission photospectrometically at 640 nm.
C) Immersing a rinsed sample as described under A) in the solution described under B) for 15 minutes at 60° C.
D) Measuring the transmission photospectrometrically at 640 nm and comparing with the transmission value measured under B).

The toluidine blue, which ionically bonds to the surface of the samples out of the solution, does not contribute to the blue color of the solution anymore. As after 15 minutes, an almost complete charge equalization on the surface can he assumed, conclusions can be made regarding the amount of negatively charged carboxylate groups based on the increase of the transmission. In this way, in experiments, a surface charge of about 700 pMol/cm² of tricarballylic acid could be measured on the samples coated as described above.

The microbiologic examination of such equipped samples, after storage for 24 hours at 37° C. in suspensions of *Escherischia coli* bacteria in physiologic saline solution, with a concentration of 1.5 million colony-forming units per ml could detect an accumulation of bacteria on the surface reduced by more than 95%.

Furthermore, silicone catheters coated with 6-aminonaphthalene-2-sulfonic acid have been artificially infected with Proteus mirabilis bacteria in pooled human urine, and tested in a model of the human urinary bladder according to Stickler (Stickler D J, Morris N S, Winters C. Simple physical model to study formation and physiology of biofilms on urethral catheters. Methods Enzymol. 1999; 310: 494-501). While uncoated silicone catheters were occluded by crystalline and organic accumulations after 40 hours already, the coated silicone catheters maintained their patency even after 96 hours.

The invention claimed is:

1. A medical product, which is either entirely or partially implantable, with a negatively charged surface for repulsing bacteria, comprising a superficially bonded substance with a permanently negative excess charge, which substance, having no pharmacological effect and with the proviso that it is not heparin, is inert against cells of the human body and the bacteria contained therein, wherein the substance carrying negative charges is a sulfonic acid having an amino group and is covalently bonded to the surface via a peptide bond and deprotonated as well as the resulting negative charge being stabilized by the establishment of a mesomerism.

2. The medical product according to claim 1, wherein the sulfonic acid used is 6-aminonaphthalene-2-sulfonic acid.

3. The medical product according to claim 1, wherein the substance is deprotonated with the help of diluted sodium hydroxide.

\* \* \* \* \*